US007172614B2

(12) United States Patent
Boyle et al.

(10) Patent No.: US 7,172,614 B2
(45) Date of Patent: Feb. 6, 2007

(54) SUPPORT STRUCTURES FOR EMBOLIC FILTERING DEVICES

(75) Inventors: William J. Boyle, Fallbrook, CA (US); John E. Papp, Temecula, CA (US); Francisco Sanchez, Temecula, CA (US); Steven T. Saville, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 438 days.

(21) Appl. No.: 10/186,258

(22) Filed: Jun. 27, 2002

(65) Prior Publication Data

US 2004/0006361 A1    Jan. 8, 2004

(51) Int. Cl.
*A61M 29/00* (2006.01)
(52) U.S. Cl. .................................... 606/200
(58) Field of Classification Search ................ 606/200, 606/113, 114, 127, 159
See application file for complete search history.

(56) References Cited

U.S. PATENT DOCUMENTS

| 3,952,747 A | 4/1976 | Kimmell, Jr. |
| 4,452,908 A | 6/1984 | Ball et al. |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |

(Continued)

FOREIGN PATENT DOCUMENTS

EP          0427429 A3      9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74.

*Primary Examiner*—Anhtuan T. Nguyen
*Assistant Examiner*—Elizabeth Houston
(74) *Attorney, Agent, or Firm*—Fulwider Patton

(57) ABSTRACT

An inner support structure for an embolic filtering device includes a tubular member having a first support region for supporting the proximal portion of a filter assembly and a second support region for supporting the distal portion of the filter assembly. The inner support structure facilitates rotation and restricts longitudinal movement of the embolic filtering device relative to a guide wire. Alternatively, the inner support structure includes a bushing coupled to the guide wire and a sleeve with a head on its proximal end positioned within a cavity in the bushing, thereby facilitating rotation and restricting longitudinal movement of the sleeve. The proximal portion of the filter assembly is supported on the sleeve. A sleeve for retaining the struts of an expandable cage of the embolic filtering device includes a central lumen for positioning the sleeve onto a guide wire and peripheral lumens for positioning and retaining the struts.

18 Claims, 6 Drawing Sheets

U.S. PATENT DOCUMENTS

| | | |
|---|---|---|
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |

| | | |
|---|---|---|
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B1 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 * | 11/2003 | Gilson et al. ............... 606/200 |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |

| Patent | Date | Inventor |
|---|---|---|
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 * | 2/2004 | Boyle et al. ............. 606/200 |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boylan et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,951,570 B2 | 10/2005 | Linder et al. |
| 6,953,471 B1 | 10/2005 | Lilly et al. |
| 6,958,074 B2 | 10/2005 | Russell |
| 6,960,370 B2 | 11/2005 | Monni et al. |
| 6,964,670 B1 | 11/2005 | Shah |
| 6,964,673 B2 | 11/2005 | Tsugita et al. |
| 6,969,395 B2 | 11/2005 | Eskuri |
| 6,969,396 B2 | 11/2005 | Krolik et al. |
| 6,972,025 B2 | 12/2005 | WasDyke |
| 6,974,468 B2 | 12/2005 | DoBrava et al. |
| 6,974,469 B2 | 12/2005 | Broome et al. |
| 6,979,344 B2 | 12/2005 | Jones et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,004,956 B2 | 2/2006 | Palmer et al. |
| 7,004,964 B2 | 2/2006 | Thompson et al. |
| 7,011,671 B2 | 3/2006 | Welch |
| 7,014,647 B2 | 3/2006 | Brady et al. |
| 7,018,393 B1 | 3/2006 | Boyle et al. |
| 7,037,320 B2 | 5/2006 | Brady et al. |
| 7,044,958 B2 | 5/2006 | Douk et al. |
| 7,048,758 B2 | 5/2006 | Boyle et al. |
| 7,097,651 B2 | 8/2006 | Harrison et al. |
| 7,097,834 B1 | 8/2006 | Boyle et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |

| | | |
|---|---|---|
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euleneuer et al. |
| 2003/0114880 A1 | 6/2003 | Hansen et al. |
| 2003/0120303 A1 | 6/2003 | Boyle et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0150821 A1 | 8/2003 | Bates et al. |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Kusleika et al. |
| 2003/0171770 A1 | 9/2003 | Anderson et al. |
| 2003/0171771 A1 | 9/2003 | Shimon |
| 2003/0171803 A1 | 9/2003 | Berrada et al. |
| 2003/0176884 A1 | 9/2003 | Broome et al. |
| 2003/0176885 A1 | 9/2003 | Wholey et al. |
| 2003/0176886 A1 | 9/2003 | Sutton et al. |
| 2003/0176889 A1 | 9/2003 | Boyle et al. |
| 2003/0181942 A1 | 9/2003 | Daniel et al. |
| 2003/0181943 A1 | 9/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195555 A1 | 10/2003 | Khairkhahan et al. |
| 2003/0199819 A1 | 10/2003 | Beck |
| 2003/0204168 A1 | 10/2003 | Bosme et aal. |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2004/0006361 A1 | 1/2004 | Boyle et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0167568 A1 | 8/2004 | Boylan et al. |
| 2004/0267301 A1 | 12/2004 | Boylan et al. |
| 2005/0004595 A1 | 1/2005 | Boyle et al. |
| 2005/0075663 A1 | 4/2005 | Boyle et al. |
| 2005/0182441 A1 | 8/2005 | Denison et al. |
| 2005/0222583 A1 | 10/2005 | Cano et al. |
| 2005/0228439 A1 | 10/2005 | Andrews et al. |
| 2006/0095069 A1 | 5/2006 | Shah et al. |
| 2006/0129183 A1 | 6/2006 | Boyle et al. |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO99/44510 | 9/1999 |
| WO | WO00/67667 | 11/2000 |
| WO | WO01/10346 | 2/2001 |
| WO | WP01/45592 | 6/2001 |
| WO | WO01/87183 | 11/2001 |

* cited by examiner

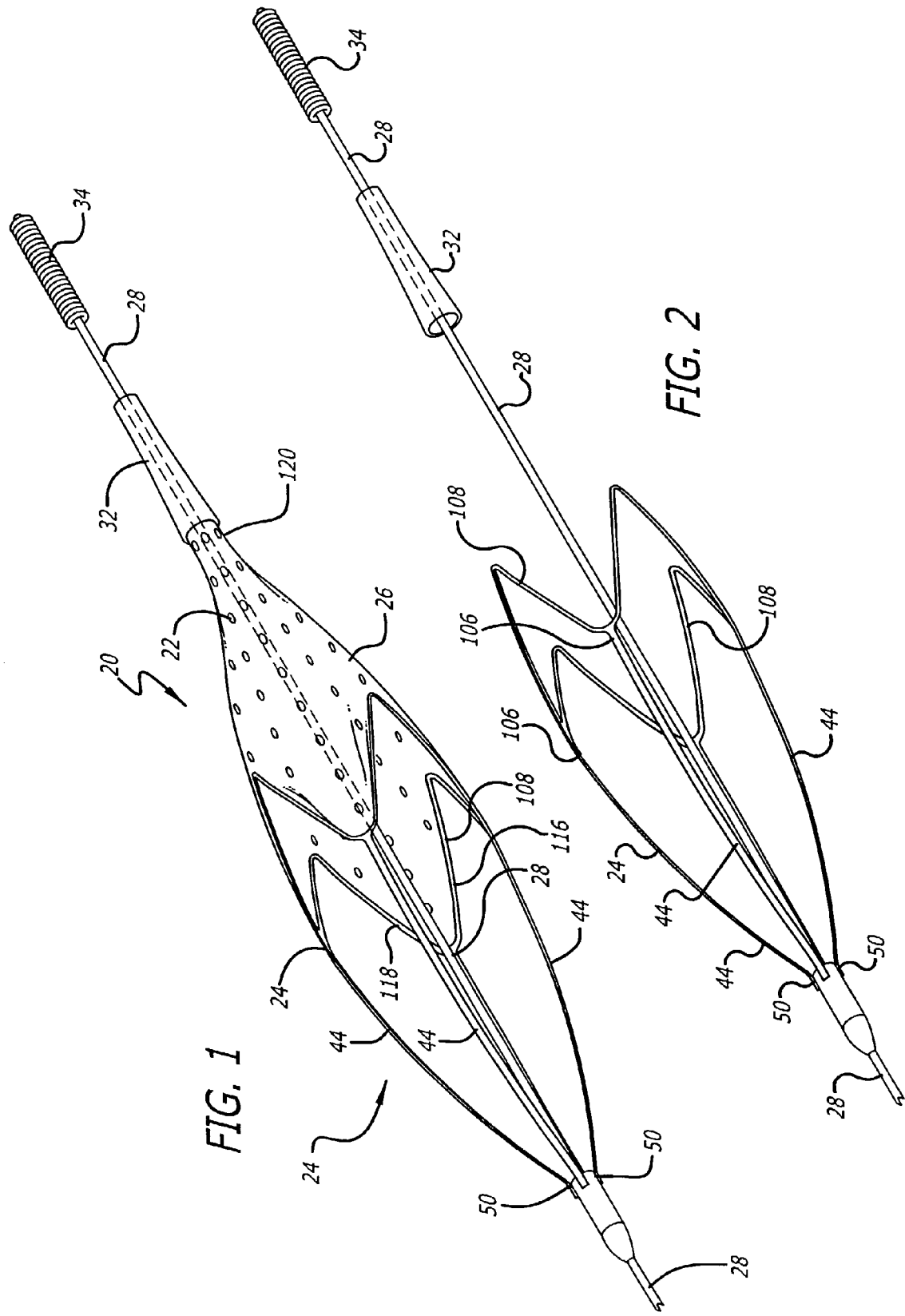

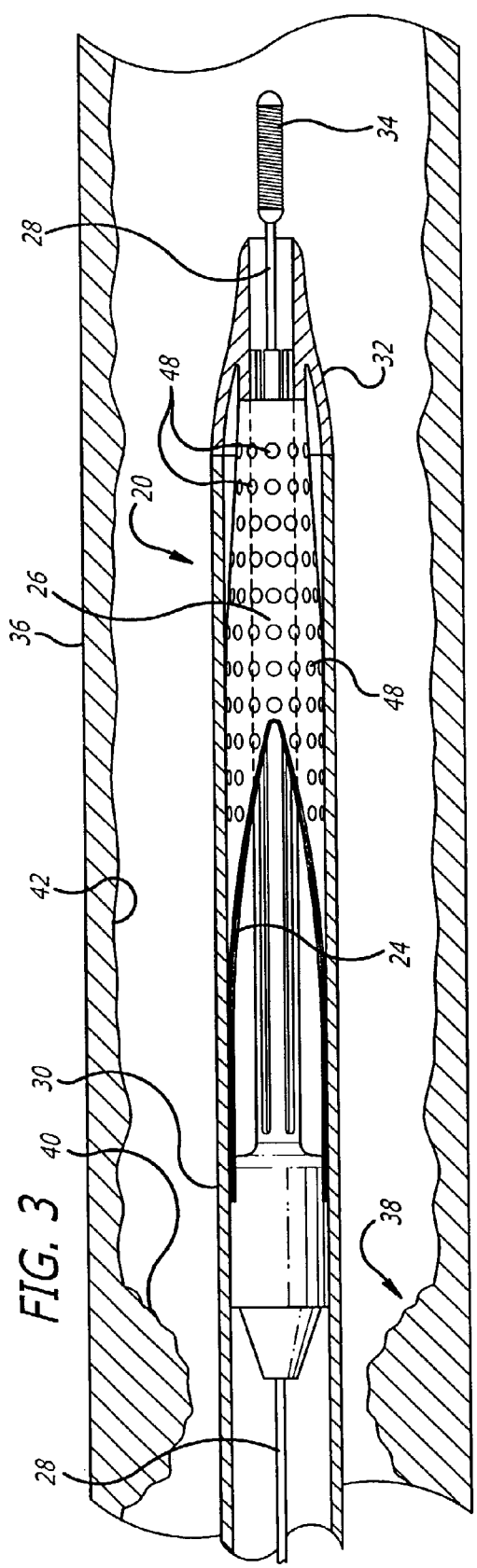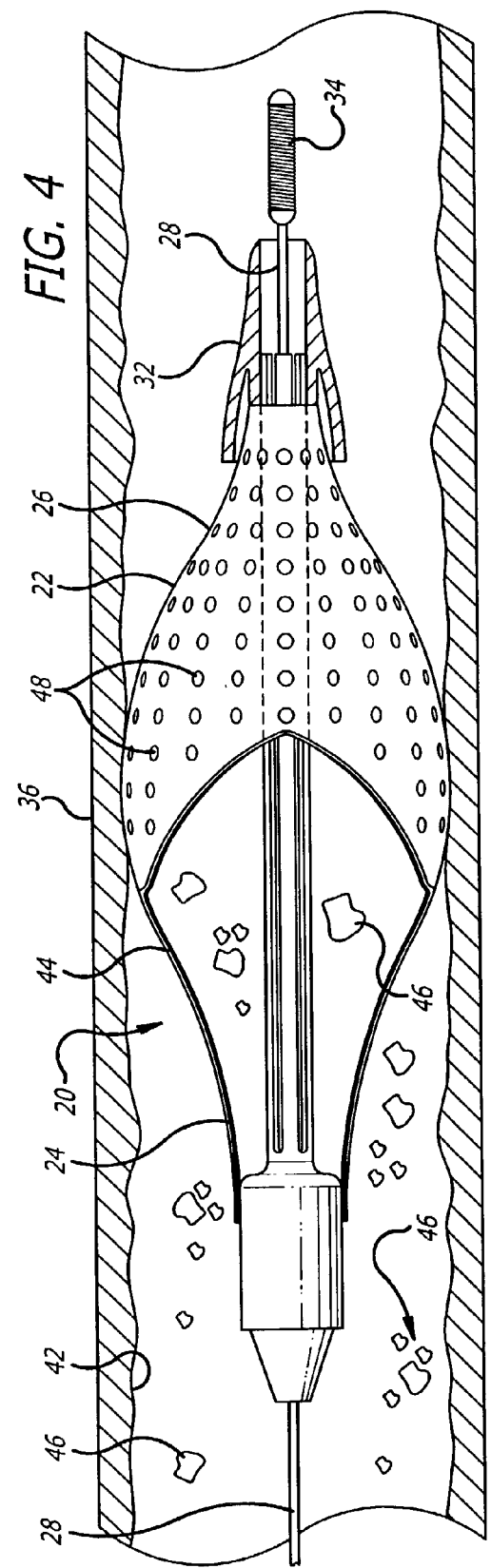

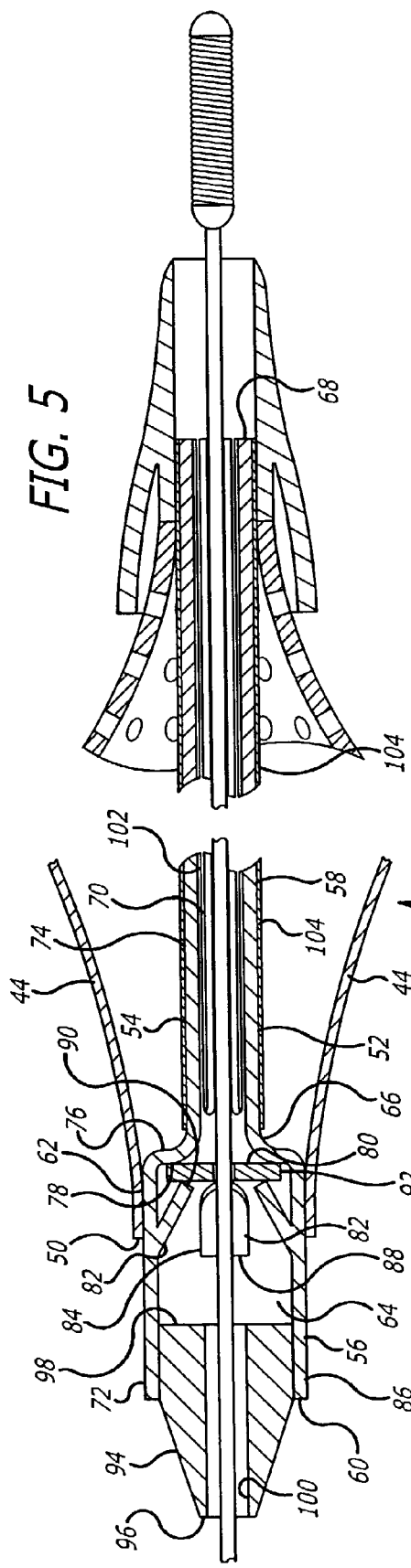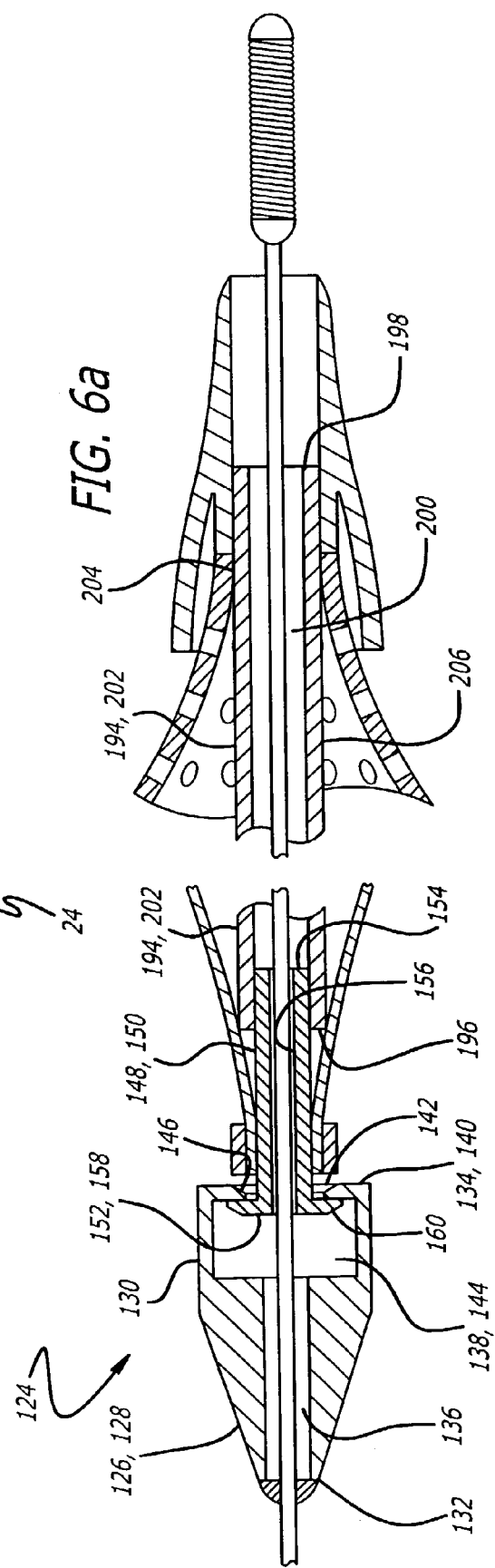

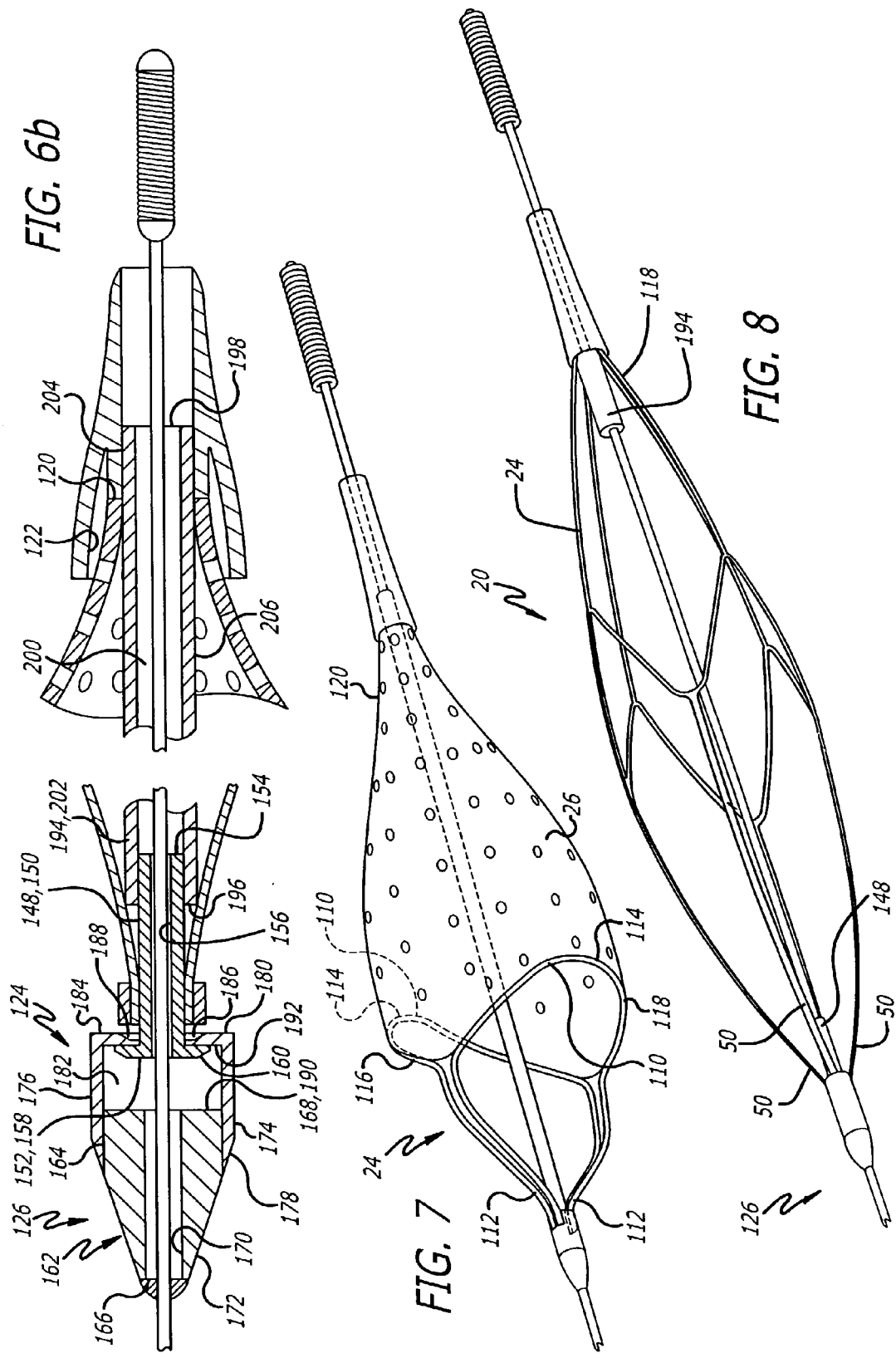

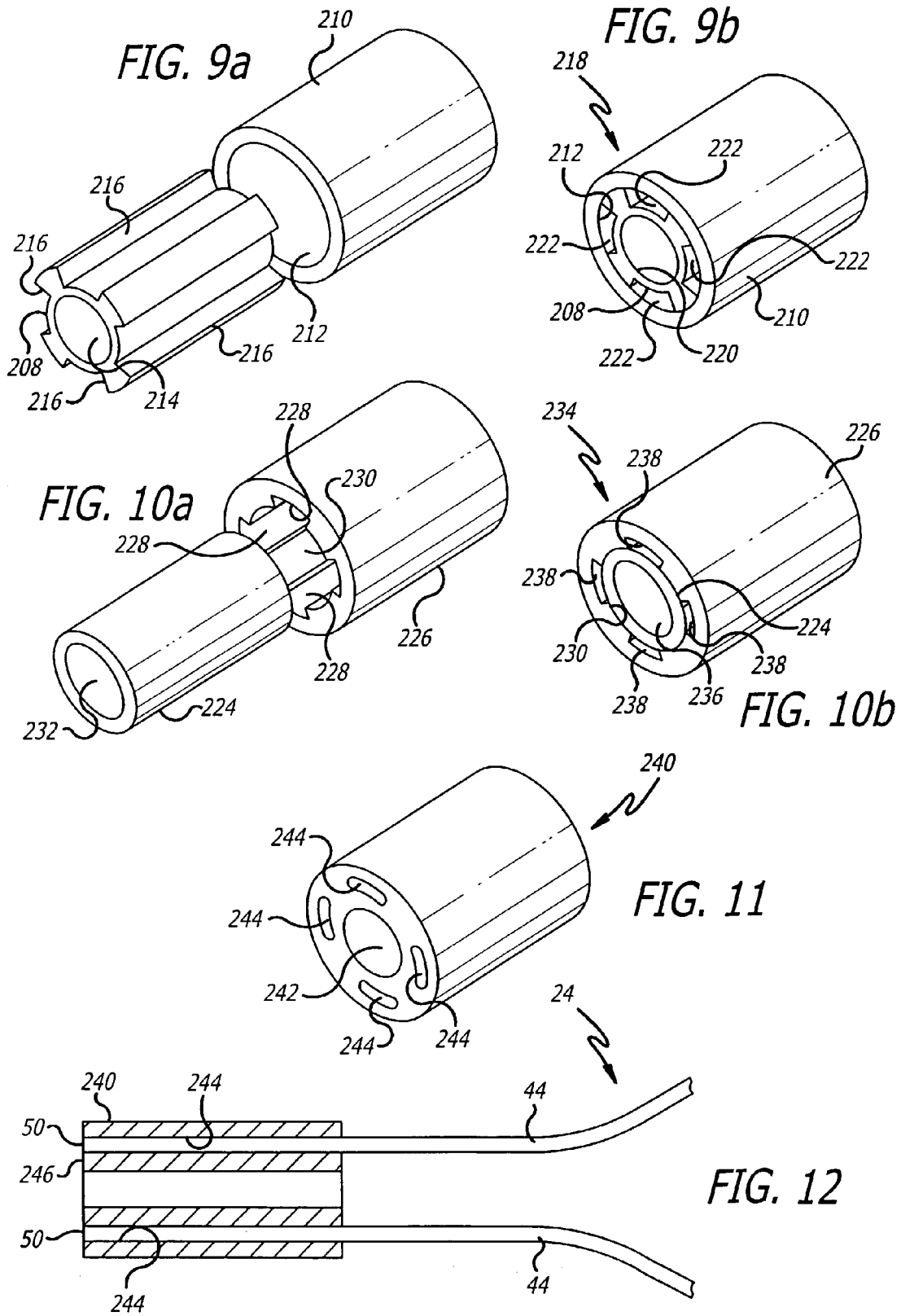

SUPPORT STRUCTURES FOR EMBOLIC FILTERING DEVICES

BACKGROUND OF THE INVENTION

The present invention relates generally to filtering devices used when an interventional procedure is being performed in a stenosed or occluded region of a body vessel to capture embolic material that may be created and released into the vessel during the procedure. The present invention is more particularly directed to a support and retention apparatus for embolic filtering devices. The present invention also is directed to an embolic filtering device having a half-basket type expandable cage which has good flexibility and bendability and allows the embolic filtering device to be readily navigated through tortuous body lumens of a patient.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter, with the trapped embolic debris, can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

Many prior art expandable filters include a cage to which a filtering element is coupled. The cage may include struts which, in turn, are coupled to a sleeve or collar mounted to the guide wire or guide wire-like member. The process for securing the struts to the sleeve is referred to herein as end termination. Current methods for terminating the ends of the struts for a cage for an embolic filtering device include sandwiching the ends of the struts of the cage between two sleeves or soldering the ends of the struts to a sleeve. The struts must first be positioned around the sleeve at desired locations and then held in place for the sandwiching or soldering operation. To achieve optimal performance of the cage, the struts should be positioned accurately. However, with the current methods of strut end termination, accuracy is sometimes difficult to achieve.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature or cause damage to the patient's vessels. As a result, there is a need to increase the flexibility of the expandable filter without compromising its structural integrity once in position within the patient's body vessel. As the lumens within the patient's vasculature are narrow, it is also preferable to minimize the size of delivery devices for expandable filters, however, the size of the delivery device is partially dictated by the size of the collapsed filter. Reducing the size of the collapsed filter and the delivery device may increase the flexibility of the delivery device. To prevent accidental or intended rotation of the guide wire from being transmitted to the deployed filtering device, it is also desirable to have the guide wire independently rotatable from the filtering device. However, when a filtering device having a half-basket support for the filter element is utilized, it is also desirable to include a continuous support structure between the proximal end and the distal end of the filter element to prevent the filter element from rotating separately from the basket and becoming tangled.

What has been needed is an expandable filter assembly having a reduced profile in the collapsed condition while maintaining structural continuity between the proximal end of the cage and the distal end of the filter to collect embolic debris which may be released into the patient's vasculature. Also, there is a need to simplify the manufacturing process for making expandable cages for embolic filtering devices. The present invention satisfies these and other needs.

SUMMARY OF THE INVENTION

The present invention provides embolic protection filters designed to have a relatively small cross profile in the collapsed condition which permits the use of a delivery catheter having a relatively small cross profile in comparison to current catheters for delivering embolic protection filters. The present invention attains a smaller cross profile while maintaining structural continuity between the proximal end of a cage portion of the filter device and the distal end of a filter element. The present invention also provides means for coupling strut portions of the cage to a delivery device.

In one aspect of the present invention, an embolic filtering device made in accordance with the present invention includes an inner support structure. The inner support structure includes a first support region, a second support region and a transition portion. The first support region includes a substantially cylindrical tubular member having an exterior surface, a first end, a second end and a cavity therebetween. The exterior surface of the first support region has a first diameter and is substantially longitudinally aligned with a longitudinal axis of the inner support structure. A cross section of the cavity of the first support region which is perpendicular to the longitudinal axis of the inner support structure has a substantially circular shape. There is also at least one deflectable tab positioned on the first support region.

The second support region includes a substantially cylindrical tubular member having an exterior surface, a first end, a second end and a lumen therebetween. At least one slot extends substantially longitudinally throughout the length of the second support region to add flexibility. The exterior surface of the second support region has a second diameter which is smaller than the first diameter of the first support region. The second support region is positioned substantially longitudinally aligned with the longitudinal axis of the inner support structure. A cross section of the lumen of the second support region which is perpendicular to the longitudinal axis of the inner support structure has a substantially circular shape which is smaller than the cross section of the cavity of the first support region.

The transition portion is coupled to the second end of the first support region and the first end of the second support region. In this manner, the transition portion forms a surface at the second end of the cavity of the first support region.

In a detailed aspect of the present invention, the slot within the second support region of the inner support structure includes four slots substantially equally spaced about a periphery of the second support region. In another detailed aspect, the inner support structure includes an elastic jacket coupled to the second support region to facilitate retaining the shape of the second support region.

In another aspect of the present invention using the inner support structure having the first and second support regions, the embolic filtering device includes an elongate guide wire having a proximal end and a distal end. A marker band is positioned on the guide wire within the distal portion of the guide wire. The inner support structure is positioned along the distal portion of the guide wire with the guide wire positioned within the cavity of the proximal support region and the lumen of the distal support region. The marker band is positioned with a clearance fit within the cavity of the proximal support region proximate the surface at the distal end of the cavity. The deflectable tab of the proximal support region is deflected radially into the cavity of the proximal support region. An apex on the deflectable tab projects into the cavity of the proximal support region at a position proximal to the marker band.

In a detailed aspect, the deflectable tab of the proximal support region of the inner support structure includes two deflectable tabs which are positioned substantially diametrically opposed to each other. The distance between the apices of the two tabs after radial deflection into the cavity of the proximal support region is smaller than the distance across the periphery of the marker band. In a further aspect, the embolic filtering device includes an annular plug having a proximal surface, a distal surface and a lumen therebetween. The guide wire is positioned within the lumen of the plug. The distal surface of the plug is positioned within the cavity of the proximal support region of the inner support structure and the plug is coupled to the cavity. A proximal surface of the plug includes an atraumatic shape.

In an additional aspect of the present invention, attachment of the embolic filtering device to a delivery device, such as a guide wire, is accomplished through a sleeve. The sleeve includes a longitudinal member having a central lumen extending substantially longitudinally throughout the length of the longitudinal member. The central lumen is sized to receive a delivery device and is positioned substantially centered along a longitudinal axis of the longitudinal member. The sleeve also includes at least one peripheral lumen which extends substantially longitudinally throughout the length of the longitudinal member and substantially parallel to the longitudinal axis of the longitudinal member. The at least one peripheral lumen is sized to receive and retain a strut of an embolic filtering device.

In a detailed aspect, the sleeve includes a substantially cylindrical shape. The at least one peripheral lumen may include four peripheral lumens substantially equally spaced about the central lumen and positioned a substantially equal distance from the longitudinal axis of the tubular member.

In another detailed aspect, the longitudinal member of the sleeve may include an outer sleeve and an inner sleeve. The outer sleeve may include a substantially cylindrical shape and a lumen throughout its length. The lumen of the outer sleeve is positioned substantially centered along a longitudinal axis of the outer sleeve. The inner sleeve may include a substantially cylindrical shape and a lumen throughout its length. The outside diameter of the inner sleeve is sized to be secured within the lumen of the outer sleeve. The lumen of the inner sleeve is sized to receive a delivery device and is positioned substantially centered along a longitudinal axis of the inner sleeve. The inner sleeve includes at least one slot which extends longitudinally along the outside surface of the inner sleeve substantially parallel to the longitudinal axis of the inner sleeve. The outer surface of the inner sleeve is coupled to the lumen surface of the outer sleeve, such that the lumen of the inner sleeve forms the central lumen of the sleeve. In this configuration, the at least one peripheral lumen is formed by the surfaces of the at least one slot on the outside surface of the inner sleeve and the lumen surface of the outer sleeve. In a more detailed aspect, the at least one slot includes four slots substantially equally spaced about the lumen of the inner sleeve. In a similar aspect, the outer sleeve includes at least one slot extending longitudinally along the surface of the lumen while the inner sleeve has no slots on its exterior surface. In this configuration, the at least one-peripheral lumen is formed by the surfaces of the at least one slot on the surface of the lumen of the outer sleeve and the outside surface of the inner sleeve. In a more detailed aspect, the at least one slot includes four slots substantially equally spaced about the lumen of the outer sleeve.

Another aspect of the present invention includes a method of coupling a strut of an embolic filtering device to a delivery device. The method includes providing a delivery device, providing a sleeve having a central lumen and at least one peripheral lumen, and providing an embolic filtering device having at least one strut. The at least one strut is inserted into and coupled to the at least one peripheral lumen of the sleeve. The delivery device is inserted into the central lumen of the sleeve and the sleeve is coupled to the delivery device.

In one detailed aspect, the strut includes an end portion having smooth surfaces and inserting the strut into the peripheral lumen includes advancing the strut through the peripheral lumen until an end of the strut is substantially flush with an end surface of the sleeve. Coupling the strut to the peripheral lumen of the sleeve includes bonding the strut to the peripheral lumen with an adhesive. In other detailed aspects, the strut may include an end portion having barbed surfaces, an end portion having perforations, and an end portion having slots through edges of the strut. Inserting the strut of any of these configurations into the peripheral lumen includes advancing the strut through the peripheral lumen until an end of the strut is substantially flush with an end surface of the sleeve. Coupling the strut to the peripheral lumen includes bonding the strut to the peripheral lumen with an adhesive.

In yet another detailed aspect, the strut includes an end portion having smooth surfaces and inserting the strut into the peripheral lumen includes advancing the strut through the peripheral lumen until an end of the strut extends out of the peripheral lumen and beyond an end surface of the sleeve. Coupling the strut to the peripheral lumen includes bonding the strut to the peripheral lumen with an adhesive within the peripheral lumen and adding a bead of the adhesive between the end portion of the strut and the end surface of the sleeve. An end portion of the strut may include an aperture on a side of the strut proximate the end of the strut so that coupling the strut to the peripheral lumen with the bead of the adhesive includes the adhesive filling the aperture in the strut.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1 is a perspective view of an embolic filtering device embodying features of the present invention.

FIG. 2 is a perspective view of the expandable cage which forms part of the embolic protection device of FIG. 1.

FIG. 3 is an elevational view, partially in cross section, of an embolic filtering device embodying features of the present invention as it is being delivered within a body vessel downstream from an area to be treated.

FIG. 4 is an elevational view, partially in cross section, similar to that shown in FIG. 3, wherein the embolic filtering device is deployed within the body vessel.

FIG. 5 is an elevational view, in cross section, of an embolic filtering device embodying features of the present invention with an apparatus for rotatably mounting the embolic filter device to a guide wire.

FIG. 6a is an elevational view, in cross section, of an embolic filtering device embodying features of the present invention with an alternative apparatus for rotatably mounting the embolic filter device to a guide wire.

FIG. 6b is an elevational view, in cross section, of an embolic filtering device embodying features of the present invention with an alternative apparatus for rotatably mounting the embolic filter device to a guide wire, similar to that shown in FIG. 6a.

FIG. 7 is a perspective view of an embolic filtering device embodying features of the present invention and having an alternative expandable cage configuration.

FIG. 8 is a perspective view of an embolic filtering device embodying features of the present invention and having a full basket expandable cage configuration.

FIG. 9a is an exploded perspective view of the components for a sleeve for retaining the struts of an embolic filtering device embodying features of the present invention.

FIG. 9b is a perspective view of the assembled sleeve for retaining the struts of an embolic filtering device including the components depicted in FIG. 9b.

FIG. 10a is an exploded perspective view of the components for a sleeve for retaining the struts of an embolic filtering device embodying features of the present invention.

FIG. 10b is a perspective view of the assembled sleeve for retaining the struts of an embolic filtering device including the components depicted in FIG. 10b.

FIG. 11 is a perspective view of a sleeve for retaining the struts of a cage of an embolic filtering device embodying features of the present invention.

FIG. 12 is a elevation view, partially in cross section, depicting the struts of a cage of an embolic filtering device coupled with a sleeve similar to that shown in FIG. 11.

DETAILED DESCRIPTION OF THE PREFERRED EMBODIMENTS

Figure 13A:
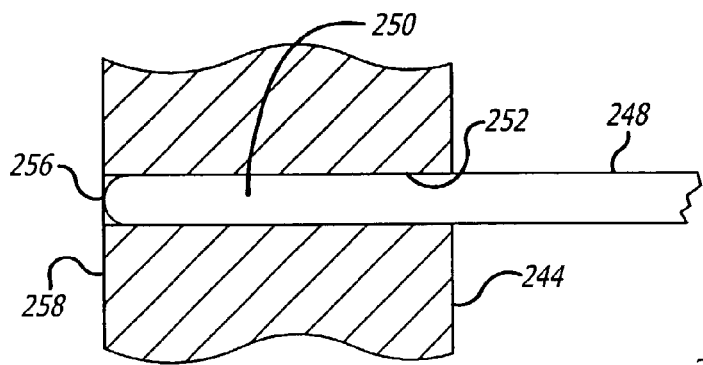
FIG. 13a is an elevational view, partially in cross section, depicting a strut of a cage of an embolic filtering device coupled with a peripheral lumen of a sleeve similar to that shown in FIG. 11.

Turning now to the drawings, in which like reference numerals represent like or corresponding elements in the drawings, FIGS. 1 and 2 illustrate one particular embodiment of an embolic filtering device 20 incorporating features of the present invention. The embolic filtering device 20 is designed to capture embolic debris which may be created and released into a body vessel during an interventional procedure. The embolic filtering device 20 includes an expandable filter assembly 22 having a self-expanding basket or cage 24 and a filter element 26 attached thereto. In this particular embodiment, the expandable filter assembly 22 is rotatably mounted onto the distal portion of a delivery device including an elongated (solid or hollow) cylindrical shaft, such as a guide wire 28. The guide wire has a proximal end (not shown) which extends outside the patient and is manipulated by the physician to deliver the filter assembly into the target area in the patient's vasculature. A restraining or delivery sheath 30 (FIG. 3) extends coaxially along the guide wire 28 in order to maintain the expandable filter assembly 22 in its collapsed position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding cage 24 immediately begins to expand within the body vessel (see FIG. 4), causing the filter element 26 to expand as well.

An obturator 32 affixed to the distal end of the filter assembly 22 can be implemented to prevent possible "snowplowing" of the embolic filtering device 20 as it is being delivered through the vasculature. The obturator can be made from a soft polymeric material, such as Pebax 40D, and includes a smooth surface to help the embolic filtering device 20 travel through the vasculature and cross lesions while preventing the distal end of the restraining sheath 30 from "digging" or "snowplowing" into the wall of the body vessel.

The guide wire 28 extends through the expandable cage 24, through the obturator 32, and to the coil tip 34 of the guide wire. The full-length guide wire allows the physician to control the proximal end of the guide wire in order to steer the distal coil tip 34 into the desired vessel when delivering the embolic filtering device 20 through the patient's vasculature.

In FIGS. 3 and 4, the embolic filtering device 20 is shown as it is being delivered within an artery 36 or other body vessel of the patient. Since the embolic filtering device 20 made in accordance with the present invention possesses excellent bendability and flexibility, it will conform well to the shape of the vasculature while allowing the filter assembly to more easily negotiate a curved radius in the patient's vasculature.

Referring now to FIG. 4, the embolic filtering device 20 is shown in its expanded position within the patient's artery 36. This portion of the artery 36 has an area of treatment 38 (FIG. 3) in which atherosclerotic plaque 40 has built up against the inside wall 42 of an artery 36 of the patient. The filter assembly 22 is to be placed distal to, and downstream from, the area of treatment 38. For example, the therapeutic interventional procedure may include the implantation of a stent (not shown) to increase the diameter of an occluded artery and increase the flow of blood therethrough. It should be appreciated that the embodiments of the embolic filtering device 20 described herein are illustrated and described by way of example only and not by way of limitation. Also, while the present invention is described in detail as applied to an artery of the patient, those skilled in the art will appreciate that it can also be used in other body vessels, such as the coronary arteries, carotid arteries, renal arteries, saphenous vein grafts and other peripheral arteries. Additionally, the present invention can be utilized when a physician performs any one of a number of interventional procedures which generally require an embolic filtering device to capture embolic debris created during the procedure, such as balloon angioplasty, laser angioplasty or atherectomy.

The cage 24 includes self-expanding struts 44 which, upon release from the restraining sheath 30, expand the filter element 26 into its deployed position within the artery 36 (FIG. 4). Embolic particles 46 created during the interventional procedure and released into the bloodstream are captured within the deployed filter element 26. The filter may include perfusion openings 48, or other suitable perfusion means, for allowing blood flow through the filter element 26. The filter element will capture embolic particles which are larger than the perfusion openings while allowing blood to perfuse downstream to vital organs. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire within the artery 36 until the balloon portion is directly in the area of treatment 38. The balloon of the dilatation catheter can be expanded, expanding the plaque 40 against the wall 42 of the artery 36 to expand the artery and reduce the blockage in the vessel at the position of the plaque. After the dilatation catheter is removed from the patient's vasculature, a stent (not shown) could be implanted in the area of treatment 38 using over-the-wire techniques to help hold and maintain this portion of the artery 36 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and should enter the filter element 26. Once the procedure is completed, the interventional device may be removed from the guide wire. The filter assembly 22 can also be collapsed and removed from the artery 36, taking with it any embolic debris trapped within the filter element 26. A recovery sheath (not shown) can be delivered over the guide wire 28 to collapse the filter assembly 22 for removal from the patient's vasculature.

The expandable cage 24 of FIGS. 1 and 2 is shown rotatably mounted to the distal portion of a delivery device, such as the guide wire 28, to allow the entire filtering assembly 22 to remain stationary once deployed in the body vessel. This feature prevents the filtering assembly from rotating in the event that the proximal end of the guide wire is accidentally rotated by the physician during use. As a result, the possibility that the deployed filtering assembly 22 could be rotated to cause trauma to the wall of the vessel is minimized. Referring specifically to FIG. 5, a first end 50 (proximal end) of the struts 44 forming the cage 24 are coupled to an inner support structure 52 which is rotatably mounted to the distal portion of the guide wire.

The inner support structure 52 may include a substantially longitudinal tubular member 54 having a first support region 56 (proximal support region) and a second support region 58 (distal support region). The proximal support region includes a first end 60 (proximal end), a second end 62 (distal end) and a cavity 64 therebetween. The distal support region includes a first end 66 (proximal end), a second end 68 (distal end) and a lumen 70 therebetween. A cross section of the proximal support region which is perpendicular to a longitudinal axis of the inner support structure is larger than a cross section of the distal support region which is perpendicular to the longitudinal axis.

In one embodiment, the proximal support region 56 and the distal support region 58 each include a substantially cylindrical shape positioned adjacent each other and substantially longitudinally aligned along the longitudinal axis of the inner support structure 52. In this embodiment, an exterior surface 72 of the proximal support region includes a first diameter and an exterior surface 74 of the distal support region includes a second diameter which is smaller than the first diameter of the proximal support region. A transition portion 76 may couple the proximal support region to the distal support region. More particularly, the transition portion couples the distal end 62 of the proximal support region to the proximal end 66 of the distal support region, thereby creating a surface 78 at the distal end of the cavity within the proximal support region.

The cavity 64 within the proximal support region 56 may be sufficiently large to house a marker band 80 which is positioned on a distal portion of the guide wire 28 with a clearance fit between the cavity and the marker band. A cross section of the cavity of the proximal support region which is perpendicular to the longitudinal axis of the inner support structure 52 may be larger than a cross section of the lumen 70 of the distal support region 58 which is perpendicular to the longitudinal axis of the inner support structure. In one embodiment, the cavity includes a substantially circular shape in a cross section that is perpendicular to the longitudinal axis of the inner support structure. The lumen of the distal support region may have a larger cross section than the guide wire such that the inner support structure can be introduced onto the guide wire with a clearance fit and be capable of rotating independently on the guide wire. In another embodiment, the lumen within the distal support region may include a circular shape in a cross section that is perpendicular to a longitudinal axis of the inner support structure.

To introduce the inner support structure 52 onto the distal portion of the guide wire 28, the guide wire may be inserted into the cavity 64 within the proximal support region 56 and into the lumen 70 within the distal support region 58. The inner support structure may be translated proximally along the guide wire until the marker band 80 on the guide wire is positioned next to the surface 78 of the cavity at the distal end 62 of the proximal support region. The lumen 70 within the distal support region 58 may be sufficiently small to prevent entry of the marker band into the lumen.

The proximal support region 56 may include at least one deflectable tab 82. To permanently retain the inner support structure 52 on the guide wire 28, the tab may be deflected radially into the cavity 64 to entrap the marker band 80 between the tab and the distal surface 78 of the cavity. The deflected tabs restrict longitudinal movement of the inner support structure on the guide wire.

The tab 82 may be formed by machining a slot 84 having a shape, such as a U-shape, through a wall 86 of the proximal support region 56 such that the slot extends from the exterior surface 72 of the proximal support region to the surface of the cavity 64. The shape of the slot may be such that the tab includes a bend line 88 forming a connecting portion positioned between two end points of the shaped slot. The distance between the two end points is sufficient to permit deflection of the tab without experiencing structural failure along the connecting portion. The distance between the connecting portion and an apex 90 of the tab is sufficient that with the tab deflected radially into the cavity, the tab creates interference with the marker band 80 and prevents removal of the inner support structure 52 from the guide wire 28. More particularly, with the tab 82 deflected radially into the cavity 64, the distance between the apex 90 of the tab and the guide wire 28 is less than the distance between a periphery 92 of the marker band 80 and the guide wire. In one embodiment, the shaped slot may be oriented longitudinally along the surface of the proximal support region. The tab is positioned longitudinally along the proximal support region such that the tab clears the marker band during deflection of the tab when assembling.

In one particular embodiment, the proximal support region 56 includes two tabs 82 positioned substantially diametrically opposed to each other. The distance between the apices 90 of the two tabs after deflection into the cavity 64 is smaller than the distance across the periphery 92 of the marker band 80. Those familiar in the art may recognize that other tab designs may be utilized with the inner support structure 52 without departing from the scope of the present invention. Accordingly, it is not intended that the invention be limited to the tab configuration disclosed herein.

An annular plug 94 having a first surface 96 (proximal surface), a second surface 98 (distal surface) and a lumen 100 therebetween may be inserted into the cavity to provide a ramp for the delivery sheath and recovery sheath to ride up on when collapsing the cage. To install the plug, the proximal end of the guide wire 28 may be inserted into the lumen in the plug and the plug translated distally along the guide wire to the proximal support region of the inner support structure 52. The plug may be retained within the cavity through methods which are well known in the art, such as bonding or an interference fit between the plug and the cavity. To provide a smooth proximal surface for the inner support structure, the proximal surface 96 of the plug 94 may include an atraumatic shape, such as a substantially conical or rounded shape. The plug may be made from a radiopaque material to facilitate tracking of the embolic filter through the patient's vasculature.

To improve flexibility through the distal support region 58 of the inner support structure 52, at least one slot 102 which extends substantially longitudinally throughout the length of the distal support region may be included. In one particular embodiment, four slots are distributed substantially equally spaced about the periphery of the distal support region. Although the slots reduce the surface area of the distal support region, sufficient material remains for the obturator 32 to be coupled to the distal portion of the distal support region through methods which are well known in the art, such as bonding. An elastic jacket 104 may be coupled to the distal support region 58 to facilitate shape retention of the distal support region having the slots during flexure of the inner support structure.

The cage 24 may include a half-basket configuration (FIGS. 1 and 2) having self-expanding struts 44 which help to deploy the filter element 26. The first ends 50 (proximal ends) of the struts may be coupled to the exterior surface 72 of the proximal support region 56 of the inner support structure 52. The second ends 106 (distal ends) of the struts are coupled to a circumferential member 108 which may be adapted to move from an unexpanded delivery position (FIG. 3) to an expanded deployed position (FIG. 4). Alternatively, in another embodiment the cage 24 may include at least one loop 110 (FIG. 7) having end portions 112 at a proximal end which may be coupled to the exterior surface 72 of the proximal support region 56, and an apex 114 at the distal end of the loop. A first end 116 (proximal end) of the filter element 26 is coupled to a distal portion 118 of the cage 24, such as at the circumferential member 108 (FIGS. 1 and 2), or to the loop 110 (FIG. 7) of the alternative embodiment. The filter element 26 tapers to a distal end 120 which is, in turn, bonded or otherwise adhesively attached to the exterior surface 74 of the distal support region 58 at a position proximate the distal end 68 of the distal support region. In one embodiment, the distal end of the filter can be bonded both to the exterior surface of the distal support region and also to a lumen 122 surface of the obturator 32, the distal end of the distal support region being positioned within the lumen of the obturator. The deployment of the cage 24 results in the filter element being placed against the wall of the artery or other body vessel preparatory to catching embolic debris within the patient's artery. The inner support structure 52 provides continuity of support between the cage 24 and the filter element 26, thereby preventing the filter element from rotating separately from the cage and becoming tangled. The inner support structure also protects the filter element by preventing the filter element from contacting the guide wire 28.

Referring specifically now to FIG. 5, the first end 50 of the struts 44 are attached to the inner support structure 52 which is rotatably mounted onto the guide wire 28. The retention method of the inner support structure allows the expandable cage 24 to spin on the guide wire but restricts the longitudinal movement of the cage on the wire. This particular mechanism is but one way to rotatably mount the expandable cage to the guide wire.

Referring to FIG. 6a, another configuration of an inner support structure 124 mechanism for rotatably mounting the expandable cage 24 to the delivery device, such as the guide wire 28, includes a stop assembly 126 coupled to a distal portion of the guide wire. The stop assembly may include a bushing portion 128 having an exterior surface 130, a first end 132 (proximal end), a second end 134 (distal end) and a lumen 136 therebetween. The exterior surface of the bushing portion may include a shape, such as a cylindrical shape, which is substantially centered about the longitudinal axis of the bushing portion. The lumen may be positioned substantially centered along a longitudinal axis of the bushing portion and sized to receive and be coupled to the guide wire 28. The exterior surface 130 toward the proximal end 132 of the bushing portion may include a conical shape.

The bushing portion 128 may include a cavity 138 positioned on a distal surface 140 at the distal end 134 of the bushing portion. The cavity may be positioned substantially centered along the longitudinal axis of the bushing portion and project into the bushing portion. The cavity may include a first region 142 (distal region) having a first periphery proximate the distal end of the bushing portion, and a second region 144 (proximal region) with a second periphery larger than the first periphery positioned adjacent the first region. An edge 146 between the distal surface of the bushing portion and the first region of the cavity may be chamferred.

The stop assembly 126 may also include a tubular sleeve 148 having an exterior surface 150, a first end 152 (proximal end), a second end 154 (distal end), and a lumen 156 therebetween. The lumen may be positioned substantially centered along a longitudinal axis of the sleeve and sized to receive a guide wire 28 with a clearance fit. The proximal end of the sleeve may include an enlarged head 158 having a periphery which is larger than the first periphery of the distal region 142 of the cavity 138 of the bushing portion 128 and smaller than the second periphery of the proximal region 144 of the cavity of the bushing portion. A length of the head 158 along the longitudinal axis of the sleeve 148 is less than a length of the proximal region of the cavity of the bushing portion along the longitudinal axis of the bushing portion 128. The exterior surface of the sleeve includes a periphery smaller than the first periphery of the distal region of the cavity of the bushing portion. Thus, the head 158 of the sleeve 148 may be positioned within the proximal region 144 of the cavity 138 of the bushing portion 128 with a clearance fit between the head of the sleeve and the cavity of the bushing portion. The second end of the sleeve projects from the cavity of the bushing portion.

In this particular embodiment, the sleeve 148 may include at least one longitudinal slot (not shown) which extends longitudinally from the proximal end 152 of the sleeve toward the distal end 154 of the sleeve to facilitate insertion of the head 158 of the sleeve into the cavity 138 of the bushing portion 128. Insertion of the head of the sleeve into the cavity of the bushing portion may be further facilitated by the inclusion of a chamfer at an outer, proximal edge 160 of the head of the sleeve. To assemble the sleeve of this embodiment with the bushing portion, the head of the sleeve is pressed against the cavity opening at the distal end of the bushing portion in a proximal direction, thereby causing the slot in the sleeve to compress and the periphery of the proximal portion of the sleeve to be reduced. When the periphery of the head is at least as small as the first periphery of the distal region of the cavity of the bushing portion, the head of the sleeve may be inserted into the second region of the cavity. Upon complete insertion of the head of the sleeve into the second region of the cavity, the head of the sleeve springs to a larger size, thereby trapping the head of the sleeve within the cavity of the bushing portion.

In an alternative embodiment (FIG. 6*b*), the bushing portion 128 of the stop assembly 126 may include a bushing 162 having an exterior surface 164, a first end 166 (proximal end), a second end 168 (distal end) and a lumen 170 therebetween. The lumen may be substantially centered along a longitudinal axis of the bushing and sized to receive and be attached to the guide wire 28. The exterior surface may include a shape, such as a cylindrical shape, which is substantially centered about the longitudinal axis of the bushing. In one embodiment, the exterior surface of the bushing toward the proximal end of the bushing may include a substantially conical shape 172 to facilitate retrieval of the embolic filtering device 20 into a sheath at the end of a surgical procedure. The bushing 162 may be coupled to the guide wire 28 through methods which are well known in the art, such as soldering or bonding.

With continued reference to FIG. 6*b*, this alternative embodiment of the stop assembly 126 also includes a tubular collar 174 having an exterior surface 176, a first end 178 (proximal end), a second end 180 (distal end), and a lumen 182 therebetween. The lumen is shaped to mate with and be coupled to the exterior surface 164 of the bushing 162. At the distal end of the collar is a ring portion 184 having an aperture 186 positioned substantially centered about the longitudinal axis of the collar. The ring portion projects inward toward the longitudinal axis of the collar and corresponds with the distal region 142 of the cavity 138 of the bushing portion. In one embodiment, the collar includes a substantially cylindrical exterior surface and a substantially circular lumen. The collar may be coupled to the bushing through methods which are well known in the art, such as soldering, bonding or through a press fit. The proximal end, of the collar may be chamferred to be flush with the conical surface of the bushing. An edge 188 between the distal surface of the collar ring portion and the inside surface of the collar ring portion may be chamferred.

Upon assembly of the bushing 162 and the collar 174 to form the bushing portion 128, the proximal end 166 of the bushing is substantially flush with the proximal end 178 of the collar and the ring portion 184 of the collar is a positioned a distance from the distal end 168 of the bushing. The cavity 138 of the bushing portion is formed by the ring portion of the collar, the lumen of the collar and a surface 190 at the second end of the bushing. With this embodiment of the stop assembly, the sleeve does not require a slot to facilitate insertion of the head of the sleeve into the cavity of the bushing portion.

To assemble the sleeve 148 with the bushing portion 128 of the alternative embodiment, the distal end 154 of the sleeve is inserted into the lumen 182 of the collar 174 and through the aperture 186 in the collar ring portion 184 such that the head 158 of the sleeve is housed within the collar lumen 182 prior to the installation of the collar onto the bushing. The collar is then coupled to the bushing, thereby trapping the head of the sleeve within the cavity 138 between the distal surface 190 of the bushing and the proximal surface 192 of the collar ring portion. In this manner, the sleeve is restricted longitudinally but can rotate freely.

The first ends 50 (proximal ends) of the struts 44 of the cage 24 may be coupled to the exterior surface 150 of the sleeve 148 of the stop assembly 126. The second ends 106 (distal ends) of the struts may be coupled to the circumferential member 108 (FIGS. 1 and 2) which is adapted to move from the unexpanded delivery position (FIG. 3) to the expanded deployed position (FIG. 4). Alternatively, in another embodiment, the cage 24 may include at least one loop 110 (FIG. 7) having proximal end portions 112 which may be coupled to the sleeve 148 of the stop assembly and an apex 114 at the distal end of the loop. The first end 116 (proximal end) of the filter element 26 is coupled to the circumferential member of the cage (FIGS. 1 and 2), or to the loop (FIG. 7) of the alternative embodiment.

To provide continuity of support between the cage 24 and the filter element 26, the inner support structure 124 also includes an inner tubular member 194 having a first end 196 (proximal end), a second end 198 (distal end) and a lumen 200 therebetween. The lumen includes a larger cross section than the guide wire 28 such that the inner tubular member can be introduced onto the guide wire with a clearance fit and be capable of rotating independently on the guide wire. In a particular embodiment, the lumen within the inner tubular member may include a circular shape in a cross section that is perpendicular to a longitudinal axis of the inner tubular member. At installation, the distal portion of the guide wire is within the lumen of the inner tubular member. A proximal portion 202 of the inner tubular member 194 is coupled to the sleeve 148 of the stop assembly 126 toward the distal end 154 of the sleeve. In one embodiment, the inner tubular member is coupled to the exterior surface 150 of the sleeve. To facilitate navigation of the embolic filter device 20 through the patient's vasculature, the inner tubular member may be fabricated from a relatively thin and flexible material, such as a polymer, a metal coil or metal braided polymer. To further facilitate navigation of the embolic filter device, the obturator 32 may be coupled to a distal portion 204 of the inner tubular member through methods which are known in the art, such as bonding with the distal end of the inner tubular member being positioned within the lumen 122 of the obturator.

The filter element 26 tapers to a distal end 120 which is, in turn, bonded or otherwise adhesively attached to an exterior surface 206 of the distal portion of the inner tubular member 194. In one embodiment, the distal end of the filter can be bonded both to the exterior surface of the distal portion of the inner tubular member and also to the lumen 122 surface of the obturator 32. The deployment of the cage 24 results in the filter element being placed against the wall of the artery or other body vessel preparatory to catching embolic debris within the patient's artery. The continuity of support between the cage 24 and the filter element 26 provided by the inner tubular member 194 prevents the filter element from rotating separately from the cage which can cause the filter element to become tangled. The inner tubular member also protects the filter element by preventing the filter element from contacting the guide wire 28.

Referring to FIG. 8, in a further embodiment utilizing the stop assembly 126 of FIGS. 6a and 6b, the cage 24 may include a full-basket configuration. In this embodiment, the embolic filtering device 20 obtains continuity of support between the cage and the filter element 26 through the cage itself. Therefore, it is not necessary for the inner tubular member 194 to be attached directly to the sleeve 148 of the stop assembly, and the inner tubular member need only be long enough to be coupled with the distal portion 118 of the cage 24, the filter element 26 and the obturator 32. As with the half-basket configuration of FIGS. 6a and 6b, the proximal ends 50 of the struts 44 of the cage are coupled to the sleeve of the stop assembly.

The inner support structure 52 of FIG. 5 or the stop assembly 126 of FIGS. 6a and 6b each provide for restriction of longitudinal movement of the cage 24 and filter element 26 at a location proximal to the cage. With the restriction of longitudinal movement controlled proximal to the cage and filter element, the distal support region 58 of the inner support structure 52 (FIG. 5) and the inner tubular member 194 (FIGS. 6a and 6b) do not carry compressive loads during retrieval of the embolic filter device 20. As a result, the only purpose of the distal support region and the inner tubular member is to prevent the filter element from rotating separately from the proximal end of the cage and to protect the filter element from the rotating guide wire 28. Therefore, the distal support region 58 (FIG. 5) and the inner tubular member 194 (FIGS. 6a and 6b) can be made from thin and flexible materials. By using thinner materials for the distal support region and the inner tubular member, and by having the restriction of longitudinal movement controlled proximal to the cage and filter, the cross profile of the collapsed filter and cage on the guide wire 28 may be reduced, which in turn permits the use of a delivery sheath having a smaller crossing profile.

The expandable cage of the present invention can be made in many ways. One particular technique for making the cage is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser. The tubing used to make the cage could possibly be made of suitable biocompatible material such as spring steel. Elgiloy is another material which could possibly be used to manufacture the cage. Also, very elastic polymers possibly could be used to manufacture the cage.

The strut size is often very small, so the tubing from which the cage is made may have a small diameter. Typically, the tubing has an outer diameter on the order of about 0.020–0.040 inches in the unexpanded condition. Also, the cage can be cut from large diameter tubing. The wall thickness of the tubing is usually about 0.076 mm (0.001–0.006 inches). As can be appreciated, the strut width and/or depth at the bending points will be less. For cages deployed in body lumens, such as PTA applications, the dimensions of the tubing may be correspondingly larger. While it is preferred that the cage be made from laser cut tubing, those skilled in the art will realize that the cage can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The cage can be laser cut much like a stent is laser cut. Details on how the tubing can be cut by a laser are found in U.S. Pat. No. 5,759,192 (Saunders), U.S. Pat. No. 5,780,807 (Saunders) and U.S. Pat. No. 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with a CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding cage made in accordance with the present invention.

In one example, the cage of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the cage such that it is super elastic at body temperature. The transformation temperature is at or below body temperature so that the cage is superelastic at body temperature. The cage is usually implanted into the target vessel which is smaller than the diameter of the cage in the expanded position so that the struts of the cage apply a force to the vessel wall to maintain the cage in its expanded position. It should be appreciated that the cage can be made from either superelastic, stress-induced martensite NiTi or shape-memory NiTi.

The cage could also be manufactured by laser cutting a large diameter tubing of nickel-titanium which would create the cage in its expanded position. Thereafter, the formed cage could be placed in its unexpanded position by back-loading the cage into a restraining sheath which will keep the device in the unexpanded position until it is ready for use. If the cage is formed in this manner, there may be no need to heat treat the tubing to achieve the final desired diameter. This process of forming the cage could be implemented when using superelastic or linear-elastic nickel-titanium.

Polymeric materials which can be utilized to create the filtering element include, but are not limited to, polyurethane and Gortex, a commercially available material. Other possible suitable materials include ePTFE. The material can be elastic or non-elastic. The wall thickness of the filtering element can be about 0.00050–0.0050 inches. The wall thickness may vary depending on the particular material selected. The material can be made into a cone or similarly sized shape utilizing blow-mold technology or dip technology. The perfusion openings 48 can be any different shape or size. A laser, a heated rod or other process can be utilized to create the perfusion openings in the filter material. The perfusion openings would, of course, be properly sized to catch the particular size of embolic debris of interest. Holes can be lazed in a spinal pattern or some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. The sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheath is placed over the filtering assembly.

Current methods for terminating the ends of the struts for a cage for an embolic filtering device include sandwiching the ends of the struts of the cage between two sleeves or soldering the ends of the struts to a sleeve. The struts must first be positioned around the sleeve and then held in place for the sandwiching or soldering operation. To achieve optimal performance of the cage, the struts should be positioned accurately. However, with the current methods of strut end termination, accuracy is difficult to achieve.

FIGS. 9a–9b, 10a–10b and 11 depict embodiments of sleeves which provide a accurate method for the end termination of the struts of cages for embolic filtering devices and other similar devices. Referring to FIG. 9a, portions of the sleeve include an inner sleeve 208 and an outer sleeve 210. The outer sleeve may include a hollow cylindrical shape having a lumen 212 throughout its length. The lumen of the outer sleeve may be positioned substantially centered along a longitudinal axis of the outer sleeve. The inner sleeve may also include a hollow cylindrical shape having a lumen 214 throughout its length, with the outside diameter of the inner sleeve being sized to be secured within the lumen of the outer sleeve and the lumen of the inner sleeve being sized to receive a delivery device, such as a guide wire (not shown). The lumen of the inner sleeve may be positioned substantially centered along a longitudinal axis of the inner sleeve. The inner sleeve includes at least one slot 216 which extends longitudinally along the exterior surface of the inner sleeve (FIG. 9a depicts four slots evenly spaced about the circumference of the inner sleeve). The inner sleeve may be substantially the same length as the outer sleeve (as shown) or alternatively longer so that the designs of FIGS. 6a and b which utilize the head 158 of the tubular sleeve 148 could also be incorporated with the embodiment of FIGS. 9a and b.

Referring to FIG. 9b, the inner sleeve 208 is inserted into the lumen 212 of the outer sleeve 210 and coupled thereto, thereby forming a single sleeve 218. The single sleeve may include a circular lumen 220 (defined by the lumen 214 of the inner sleeve) along a longitudinal axis of the sleeve. The single sleeve may also include at least one peripheral lumen 222 defined by the at least one slot 216 on the inner sleeve and the surface of the lumen 212 of the outer sleeve. The peripheral lumens are sized to receive and retain struts of a cage for an embolic filtering device, or other similar device.

FIG. 10a depicts portions of a sleeve including an inner sleeve 224 and an outer sleeve 226 which is similar to the sleeve of FIGS. 9a and 9b. However, in this embodiment the outer sleeve may include a hollow cylindrical shape which includes at least one slot 228 which extends longitudinally along the surface of the lumen 230 of the outer sleeve (FIG. 10a depicts four slots evenly spaced about the circumference of the lumen of the outer sleeve). The inner sleeve 224 may also include a hollow cylindrical shape having a lumen 232, with the outside diameter of the inner sleeve being sized to be secured within the lumen of the outer sleeve and the lumen of the inner sleeve being sized to receive a delivery device, such as a guide wire (not shown). The inner sleeve may be substantially the same length as the outer sleeve (as shown) or alternatively longer so that the designs of FIGS. 6a and b which utilize the head 158 of the tubular sleeve 148 could also be incorporated with the embodiment of FIGS. 10a and b.

Referring to FIG. 10b, the inner sleeve 224 is inserted into the lumen 230 of the outer sleeve 226 and coupled thereto, thereby forming a single sleeve 234. The single sleeve may include a circular lumen 236 (defined by the lumen 232 of the inner sleeve) along a longitudinal axis of the sleeve. The single sleeve may also include at least one peripheral lumen 238 defined by the at least one slot 228 on the lumen of the outer sleeve and the external surface of the inner sleeve. The peripheral lumens are sized to receive and retain struts of a cage for an embolic filtering device, or other similar device.

FIG. 11 depicts a single sleeve 240 including a hollow cylindrical shape with a central lumen 242 extending along a longitudinal axis of the sleeve. The central lumen is sized to receive a delivery device, such as a guide wire (not shown). The sleeve may also include at least one peripheral lumen 244 (FIG. 11a depicts four peripheral lumens substantially equally spaced about the longitudinal axis with each peripheral lumen positioned a substantially equal distance radially from the longitudinal axis). The peripheral lumens are sized to receive and retain struts of a cage for an embolic filtering device, or other similar device.

FIG. 12 depicts the struts 44 of the cage 24 inserted into the peripheral lumens 244 of the sleeve 240 of FIG. 11. Using the sleeve of the depicted embodiment, each of the struts is confined to the radial and angular location dictated by a corresponding peripheral lumen. The longitudinal location of the struts may also be controlled, such as by positioning the first end 50 of each of the struts substantially flush with an end surface 246 of the sleeve.

FIGS. 13a–13e depict methods of coupling the struts to a sleeve. For example, FIG. 13a depicts a strut 248 having smooth surfaces within an end portion 250 of the strut. The end portion is positioned within a peripheral lumen 252 of a sleeve 254. An end 256 of the strut is depicted flush with an end surface 258 of the sleeve. The strut of this embodiment may be coupled to the sleeve through means which are well known in the art, such as by soldering or adhesive bonding.

Figure 13B:
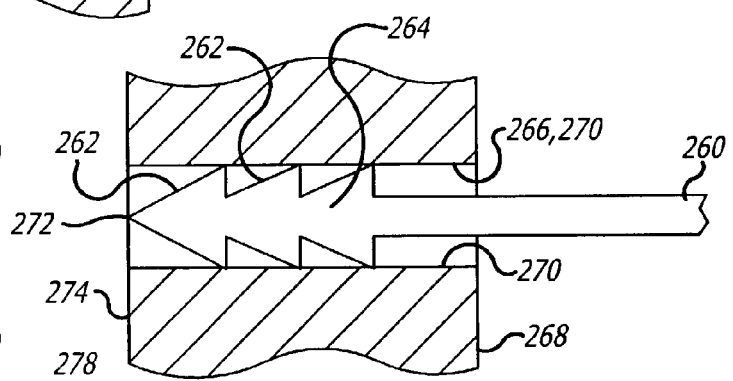
FIG. 13b is an elevational view, partially in cross section, depicting a strut of a cage of an embolic filtering device coupled with a peripheral lumen of a sleeve similar to that shown in FIG. 11.

FIG. 13b depicts sides of a strut 260 having barbed surfaces 262 within an end portion 264 of the strut. The barbed end portion of the strut is inserted into a peripheral lumen 266 of a sleeve 268 with the barbs positioned adjacent to walls 270 of the peripheral lumen. An end 272 of the strut is depicted flush with an end surface 274 of the sleeve. The barbs facilitate retention of the strut within the peripheral lumen. To further ensure retention of the barbed strut within the peripheral lumen, the strut may be coupled to the sleeve through means which are well known in the art, such as be soldering or adhesive bonding. Alternatively, the barbs may interfere with the surfaces 270 and bite into the material for retension.

Figure 13C:
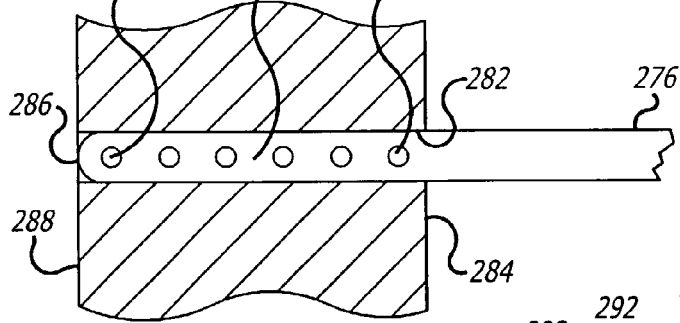
FIG. 13c is an elevational view, partially in cross section, depicting a strut of a cage of an embolic filtering device coupled with a peripheral lumen of a sleeve similar to that shown in FIG. 11.

FIG. 13c depicts a strut 276 having perforations 278 within an end portion 280 of the strut. The perforated end portion of the strut is positioned within a peripheral lumen 282 of a sleeve 284. An end 286 of the strut is depicted flush with an end surface 288 of the sleeve. The strut of this embodiment may be coupled to the sleeve through means which are well known in the art, such as by adhesive bonding. When adhesive bonding is used, the adhesive may flow into and fill the perforations, thereby aiding retention of the strut within the peripheral lumen.

Figure 13D:
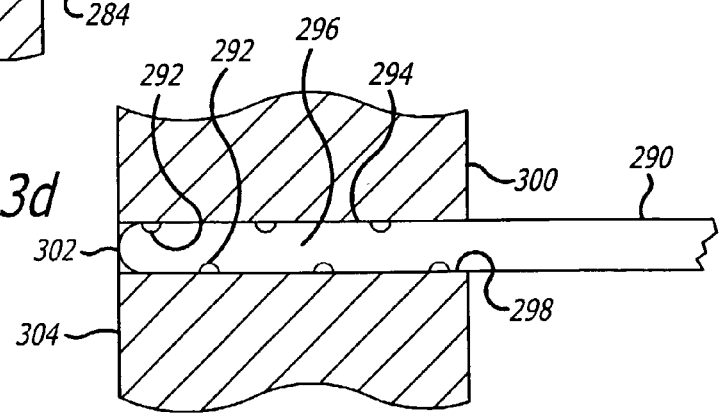
FIG. 13d is an elevational view, partially in cross section, depicting a strut of a cage of an embolic filtering device coupled with a peripheral lumen of a sleeve similar to that shown in FIG. 11.

FIG. 13d depicts a strut 290 having slots 292 through the edges 294 within an end portion 296 of the strut. The slotted end portion of the strut is positioned within a peripheral lumen 298 of a sleeve 300. An end 302 of the strut is depicted flush with an end surface 304 of the sleeve. The strut of this embodiment may be coupled to the sleeve through means which are well known in the art, such as by adhesive bonding. When adhesive bonding is used, the adhesive may flow into and fill the slots, thereby aiding retention of the strut within the peripheral lumen.

Figure 13E:
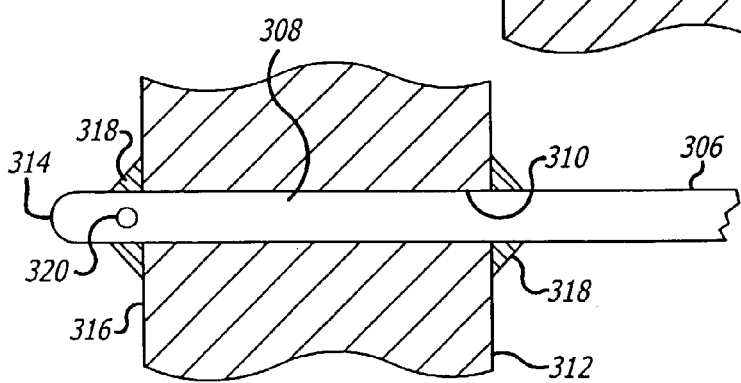
FIG. 13e is an elevational view, partially in cross section, depicting a strut of a cage of an embolic filtering device coupled with a peripheral lumen of a sleeve similar to that shown in FIG. 11.

FIG. 13e depicts a strut 306 having smooth surfaces within an end portion 308 of the strut. The end portion is positioned within a peripheral lumen 310 of a sleeve 312. An end 314 of the strut extends out of the peripheral lumen and beyond an end surface 316 of the sleeve. The strut of this embodiment may be coupled to the sleeve through means which are well known in the art, such as by adhesive bonding. When adhesive bonding is used, a bead 318 of the adhesive may be added between the end surface of the sleeve and the portion of the strut which extends beyond the end surface of the sleeve. To further facilitate retention of the strut within the peripheral lumen, an end portion of the strut may include an aperture 320 on a side of the strut proximate the end. The adhesive within the bead may flow into and fill the aperture.

Further modifications and improvements may additionally be made to the device and method disclosed herein without departing from the scope of the present invention. Accordingly, it is not intended that the invention be limited, except as by the appended claims.

What is claimed:

1. An inner support structure for an embolic filtering device, the inner support structure comprising:
    a first support region positioned substantially longitudinally aligned with a longitudinal axis of the inner support structure, the first support region including a substantially longitudinal tubular member having an exterior surface, a first end, a second end and a cavity therebetween;
    a second support region positioned substantially longitudinally aligned with the longitudinal axis of the inner support structure, the second support region including a substantially longitudinal tubular member having an exterior surface, a first end, a second end and a lumen therebetween, a cross section of the exterior surface of the second support region which is perpendicular to the longitudinal axis of the inner support structure being smaller than a cross section of the exterior surface of the first support region which is perpendicular to the longitudinal axis of the inner support structure;
    a transition portion coupled to the second end of the first support region and the first end of the second support region, the transition portion forming a surface at the second end of the cavity of the first support region; and
    at least one deflectable tab positioned on the first support region which is adapted to lock the inner support structure to a guide wire.

2. The inner support structure of claim 1, wherein:
    the first support region includes a substantially cylindrical shape, the exterior surface of the first support region having a first diameter; and
    the second support region includes a substantially cylindrical shape, the exterior surface of the second support region having a second diameter which is smaller than the first diameter of the first support region.

3. The inner support structure of claim 1, wherein a cross section of the cavity of the first support region which is perpendicular to the longitudinal axis of the inner support structure is larger than a cross section of the lumen of the second support region which is perpendicular to the longitudinal axis of the inner support structure.

4. The inner support structure of claim 3, the cross section of the cavity of the first support region having a substantially circular shape.

5. The inner support structure of claim 3, the cross section of the lumen of the second support region having a substantially circular shape.

6. An inner support structure for an embolic filtering device, the inner support structure comprising:
    a first support region positioned substantially longitudinally aligned with a longitudinal axis of the inner support structure, the first support region including a substantially longitudinal tubular member having an exterior surface, a first end, a second end and a cavity therebetween;
    a second support region positioned substantially longitudinally aligned with the longitudinal axis of the inner support structure, the second support region including a substantially longitudinal tubular member having an exterior surface, a first end, a second end and a lumen therebetween, a cross section of the exterior surface of the second support region which is perpendicular to the longitudinal axis of the inner support structure being smaller than a cross section of the exterior surface of the first support region which is perpendicular to the longitudinal axis of the inner support structure;
    a transition portion coupled to the second end of the first support region and the first end of the second support region, the transition portion forming a surface at the second end of the cavity of the first support region;
    at least one deflectable tab positioned on the first support region which is adapted to lock the inner support structure to a guide wire; and
    at least one slot extending substantially longitudinally throughout the length of the second support region.

7. The inner support structure of claim 6, the at least one slot comprising four slots substantially equally spaced about a periphery of the second support region.

8. The inner support structure of claim 6, further comprising an elastic jacket coupled to the second support region.

9. An inner support structure for an embolic filtering device, the inner support structure comprising:
    a first support region including a substantially cylindrical tubular member having an exterior surface, a first end, a second end and a cavity therebetween, the exterior surface of the first support region having a first diameter, the first support region being substantially longitudinally aligned with a longitudinal axis of the inner support structure, a cross section of the cavity of the first support region which is perpendicular to the longitudinal axis of the inner support structure having a substantially circular shape;

a second support region including a substantially cylindrical tubular member having an exterior surface, a first end, a second end, a lumen therebetween, and at least one slot extending substantially longitudinally throughout the length of the second support region, the exterior surface of the second support region having a second diameter which is smaller than the first diameter of the first support region, the second support region being substantially longitudinally aligned with the longitudinal axis of the inner support structure, a cross section of the lumen of the second support region which is perpendicular to the longitudinal axis of the inner support structure having a substantially circular shape which is smaller than the cross section of the cavity of the first support region;

a transition portion coupled to the second end of the first support region and the first end of the second support region, the transition portion forming a surface at the second end of the cavity of the first support region; and at least one deflectable tab positioned on the first support region which is adapted to lock the inner support structure to a guide wire.

10. The inner support structure of claim 9, further comprising an elastic jacket coupled to the second support region.

11. An embolic filtering device, comprising:

an elongate guide wire including a proximal end and a distal end;

a marker band positioned on the guide wire within the distal portion of the guide wire; and an inner support structure rotatably mounted onto the distal portion of the guide wire, the inner support structure including, a proximal support region having a substantially cylindrical tubular member with an exterior surface, a proximal end, a distal end and a cavity therebetween, the exterior surface of the proximal support region having a first diameter, the proximal support region being substantially longitudinally aligned with a longitudinal axis of the inner support structure, a distal support region including a substantially cylindrical tubular member having an exterior surface, a proximal end, a distal end and a lumen therebetween, the exterior surface of the distal support region having a second diameter which is smaller than the first diameter of the proximal support region, the distal support region being substantially longitudinally aligned with the longitudinal axis of the inner support structure, a transition portion coupled to the distal end of the proximal support region and the proximal end of the distal support region, the transition portion forming a surface at the distal end of the cavity of the proximal support region, and at least one deflectable tab positioned on the proximal support region;

wherein the inner support structure is positioned along the distal portion of the guide wire, the guide wire is positioned within the cavity of the proximal support region and the lumen of the distal support region, the marker band is positioned within the cavity of the proximal support region proximate the surface at the distal end of the cavity of the proximal support region; and wherein the at least one deflectable tab of the proximal support region is deflected radially into the cavity of the proximal support region, and an apex on the at least one deflectable tab projects into the cavity of the proximal support region at a position proximal to the marker band.

12. The embohic filtering device of claim 11, the distal support region of the inner support structure further comprising at least one slot extending substantially longitudinally throughout the length of the distal support region.

13. The embohic filtering device of claim 12, the at least one slot comprising four slots substantially equally spaced about a periphery of the distal support region.

14. The embolic filtering device of claim 12, further comprising an elastic jacket coupled to the distal support region.

15. The embolic filtering device of claim 11, the at least one deflectable tab of the proximal support region of the inner support structure comprising two deflectable tabs positioned substantially diametrically opposed to each other, the distance between the apices of the two tabs after radial deflection into the cavity of the proximal support region being smaller than the distance across the periphery of the marker band.

16. The embolic filtering device of claim 11, the at least one tab of the proximal support region of the inner support structure being positioned longitudinally on the proximal support region such that there is clearance between the at least one tab and the marker band during deflection of the at least one tab.

17. The embolic filtering device of claim 11, further comprising an annular plug having a proximal surface, a distal surface and a lumen therebetween, wherein the guide wire is positioned within the lumen of the plug, the distal surface of the plug is positioned within the cavity of the proximal support region of the inner support structure, the plug is coupled to the cavity of the proximal support region, and a proximal surface of the plug includes an atraumatic shape.

18. The embolic filtering device of claim 17, the plug further comprising a radiopaque material.

* * * * *

UNITED STATES PATENT AND TRADEMARK OFFICE
CERTIFICATE OF CORRECTION

PATENT NO. : 7,172,614 B2  Page 1 of 1
APPLICATION NO. : 10/186258
DATED : February 6, 2007
INVENTOR(S) : William J. Boyle et al.

It is certified that error appears in the above-identified patent and that said Letters Patent is hereby corrected as shown below:

Title Page Item (56), Page 2, Column 2,
Insert --6,209,710   9/2001   Cryer et al-- after "6,206,868   3/2001   Parodi".

Title Page Item (56), Page 4, Column 2,
Insert --7,097,440   8/2006   Boyle et al-- after "7,048,758   5/2006 Boyle et al".

Title Page Item (56), Page 5, Column 1,
Insert --2003/0130686   7/2003   Daniel et al-- after "2003/0105484 6/2003   Boyle et al".

Column 5,
Line 57, change "one-peripheral" to --one peripheral--.

Signed and Sealed this

Seventeenth Day of April, 2007

JON W. DUDAS
*Director of the United States Patent and Trademark Office*